United States Patent [19]
Garrison

[11] 3,998,214
[45] Dec. 21, 1976

[54] PREMATURE VENTRICULAR CONTRACTION DETECTOR AND METHOD
[75] Inventor: Lynn R. Garrison, Alsip, Ill.
[73] Assignee: Brondy Laboratories, Inc., Palos Heights, Ill.
[22] Filed: May 19, 1975
[21] Appl. No.: 578,367
[52] U.S. Cl. .................................... 128/2.06 A
[51] Int. Cl.² .................................... A61B 5/04
[58] Field of Search .............. 128/2.05 P, 2.05 R, 128/2.05 T, 2.06 A, 2.06 F, 2.06 R

[56] References Cited
UNITED STATES PATENTS

| | | | |
|---|---|---|---|
| 3,590,811 | 7/1971 | Harris | 128/2.06 R |
| 3,599,628 | 8/1971 | Abbenante et al. | 128/2.06 F |
| 3,613,670 | 10/1971 | Edenhofer | 128/2.06 F |
| 3,828,768 | 8/1974 | Douglas | 128/2.06 A |

Primary Examiner—William E. Kamm
Attorney, Agent, or Firm—Edmond T. Patnaude

[57] ABSTRACT

Premature ventricular contractions are detected by separately rectifying the high and low frequency components of the QRS portion of an ECG waveform, integrating the rectified high frequency signal and using such integral to control the gain of an AGC input circuit, and comparing such integral with the rectified low frequency signal to provide an output signal indicating the occurrence of a PVC.

9 Claims, 4 Drawing Figures

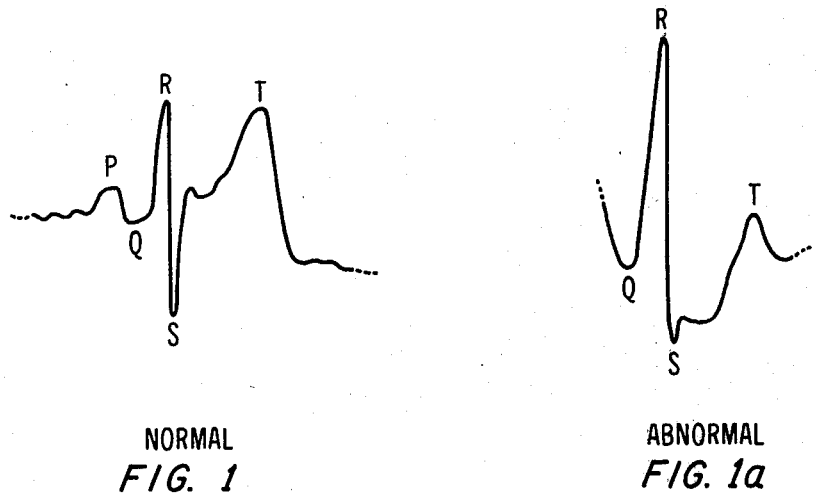
NORMAL
FIG. 1
ABNORMAL
FIG. 1a
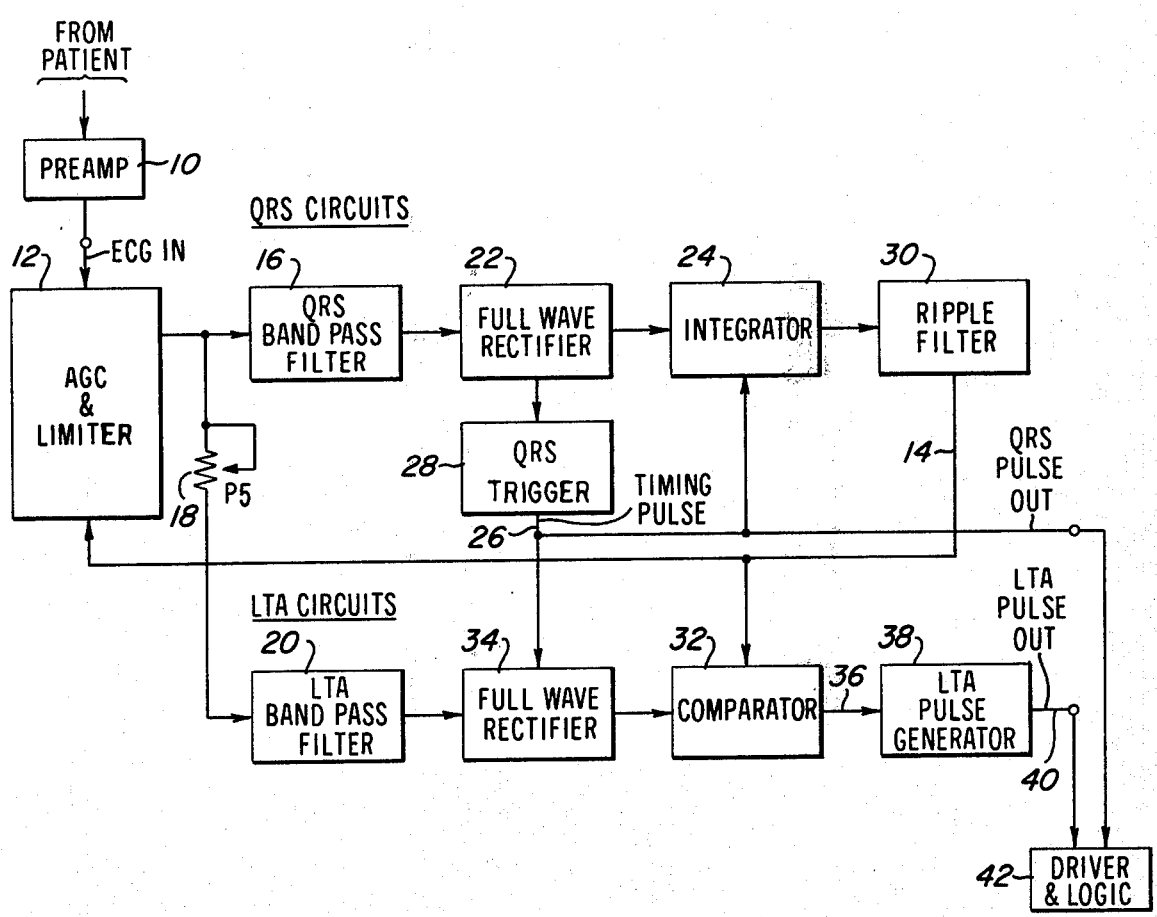
FIG. 2

PREMATURE VENTRICULAR CONTRACTION DETECTOR AND METHOD

The present invention relates in general to the art of monitoring the muscular action of the heart, and it relates more particularly to a method and instrument for monitoring an ECG waveform from a patient to detect the presence of cardiac arrhythmias.

BACKGROUND OF THE INVENTION

In order to observe the muscular action of the heart it is well known to attach electrodes to the body of a patient so as to obtain a continuous electric signal representing the muscular activity of the heart. When this signal is plotted or displayed relative to a linear time base there is provided an ECG waveform having certain characteristic points identified as P, Q, R, S and T. The Q, R, S portion of the ECG waveform is known as the QRS complex and its shape is indicative of normal or abnormal cardiac behavior.

Certain types of abnormal cardiac behavior indicate an imminent threat to the life of the patient and include premature ventricular contraction, commonly known as PVC. PVCs are made manifest by an irregularity in the QRS complex. The frequency at which PVCs occur is important since, for example, while one or two irregular PVC beats per minute may not present any immediate danger, five or more per minute indicates that the heart is likely to go into fibrillation at any time. While it is possible to visually observe an ECG waveform and detect the presence of PVCs, personnel having the necessary training and skill are not generally available. Moreover, constant personal observation of the waveform is both tedious and expensive.

There is disclosed in U.S. Pat. No. 3,828,768 a system for differentiating between a QRS complex corresponding to normal heart action and a QRS complex corresponding to abnormal heart action of the types indicating an immediate threat to the life of the patient. In the system disclosed in the said patent, the ECG signal from the patient is applied to high and low bandpass filters to separate the high and low frequency components of the signal. For a period of time including the QRS interval, the output from the low pass filter is gated to an integrator from which the integral is coupled to a comparator for comparison thereof with a manually set reference standard. An alarm is triggered and a PVC recorded each time the integral of the low frequency components of the QRS complex exceeds the reference standard.

While that patented system functions satisfactorily under certain controlled conditions, it is sensitive to extraneous muscular activities and movements of the patient which cause irregularities in the ECG waveform of the type generally known as artifacts. Also, the manner in which the length of the gating signal is determined permits improper triggering of the integrator. Consequently, false PVC detections are common with the system disclosed in the said patent.

OBJECTS OF THE INVENTION

Therefore, an object of the present invention is to provide an improved method and system for detecting cardiac arrhythmias, which system is relatively insensitive to artifacts in the ECG waveform of a patient.

SUMMARY OF THE INVENTION

Briefly, in accordance with the teachings of the present invention there is provided an ECG wave monitor which integrates the rectified high frequency components of the QRS complex to provide a feedback signal for a novel AGC circuit through which the ECG signal initially passes thereby to render the circuit substantially insensitive to overall changes in the amplitude of the ECG wave. The AGC circuit also functions to limit the amplitude of the ECG wave applied to the sensing circuits thereby rendering the instrument relatively insensitive to amplitude bursts of the type associated with patient movement and muscular artifacts. PVCs are sensed by comparing the amplitudes of the rectified high and low frequency components of the ECG wave only during occurrence of the QRS complex by means of a novel timing circuit which helps prevent false triggering of the gating circuit.

BRIEF DESCRIPTION OF THE DRAWINGS

Further objects and advantages and a better understanding of the present invention can be had by reference to the following detailed description, wherein:

FIG. 1s is a normal ECG waveform;

FIG. 1b is an ECG waveform including a PVC:

FIG. 2 is a block diagram of an ECG monitor embodying the present invention.

DETAILED DESCRIPTION OF THE DRAWINGS

Figure 3:
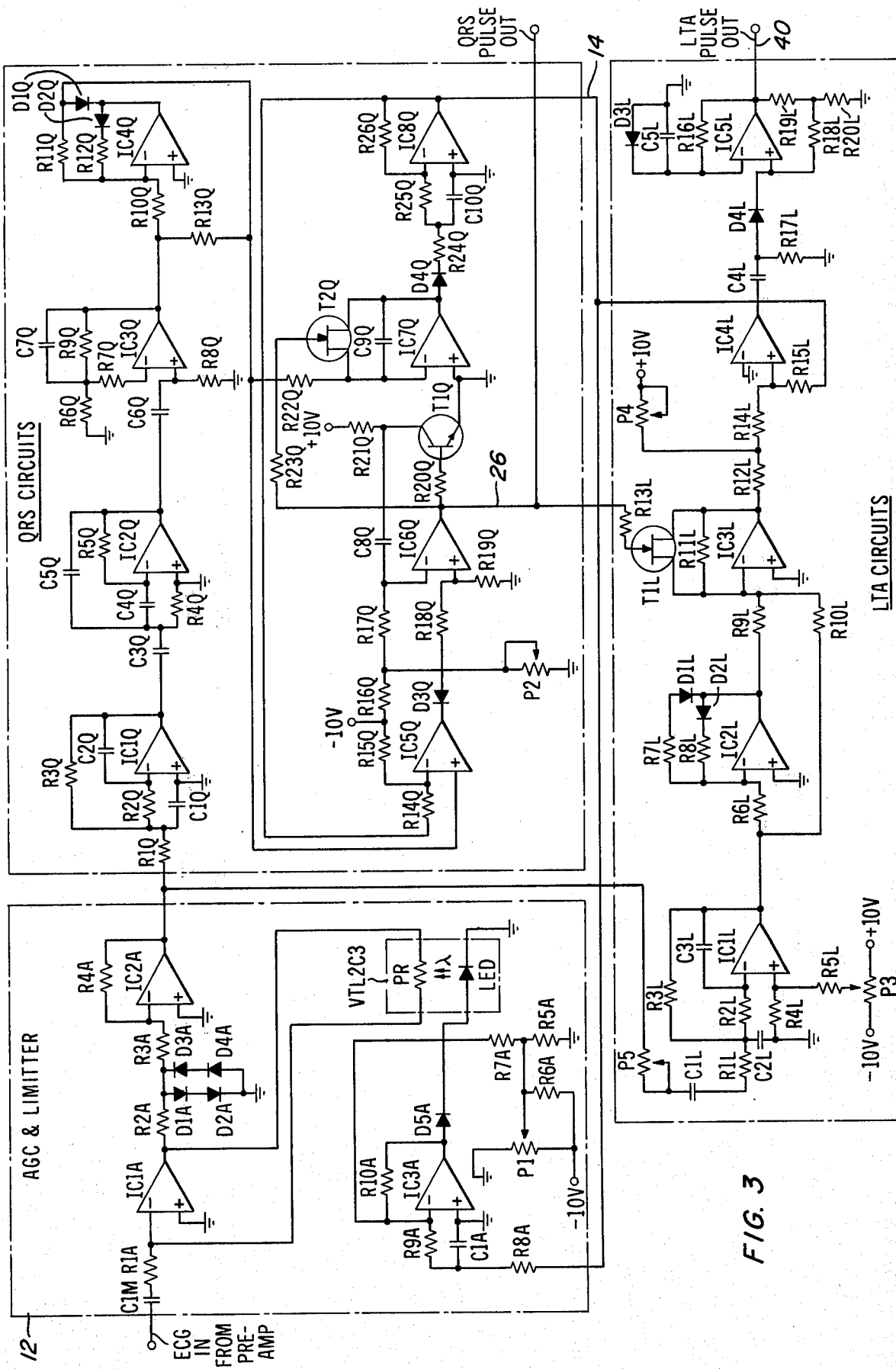
FIG. 3 is a schematic circuit diagram of the monitor of FIG. 2.

Referring now to the drawings and particularly to FIGS. 1a and 1b, there is shown in FIG. 1a that portion of an ECG waveform including a normal QRS complex while in FIG. 1b there is shown the same portion of an ECG waveform including an abnormal QRS complex of the type commonly known as a PVC. It may be seen from inspection of these two waveforms that when a PVC occurs the R peak is substantially greater than normal, and the S portion of the waveform is of considerably longer duration than normal. While all PVCs are not of the same shape, they differ from normal heartbeats and their presence is characterized by R peaks of usually greater than normal amplitude and QRS segments of greater than normal duration. The purpose of the present invention is to accurately and automatically detect each and every PVC without giving false indications when PVCs are not present.

Referring to FIG. 2 wherein the PVC detector of the present invention is shown in block diagram form, the signal from the patient is amplified in a preamplifier 10 and coupled to an AGC and limiter circuit 12 whose gain is controlled by a feedback voltage applied thereto through a conductor 14. The output of the AGC circuit is an EGC waveform of relatively constant average voltage from which spurious artifacts have been removed by the limiter. This output is coupled to a high frequency band-pass filter 16 and also coupled through a variable resistor 18 to a low frequency band-pass filter 20. The high frequency signal passed by the filter 16 is referred to herein as the QRS wave and the low frequency signal passed by the filter 20 is referred to herein as the LTA wave.

The QRS band-pass filter 16 has a passband of about 10 Hz to 17 Hz while the LTA band-pass filter 20 has a passband of about 1.5 to 6 Hz. These two filters have a gain of about −6dB at the high and low ends of the respective bands and peak about midway in the bands.

The QRS wave from the filter 16 is applied to a full wave rectifier 22 whose output drives an integrator 24. The integrator functions to integrate only the QRS portion of the ECG wave during each heartbeat, wherefor a timing or gating pulse is supplied to the integrator 24 via a conductor 26. As more fully described hereinafter, the gating pulse is produced by a QRS trigger circuit 28 which responds to an output from the QRS rectifier 22. The QRS trigger pulse causes the integrator to integrate for a period of approximately 120 msec commencing with the initiation of the R peak. To help prevent false triggering on subsequent peaks in an irregular heartbeat, a time delay circuit is provided to keep the circuit 28 from again triggering for a period of approximately 80 to 100 msec after it initially triggers.

The output of the integrator 24 is a dc signal and is passed through a ripple filter 30 before being coupled to one input of a comparator 32. The output of the integrator 24 is also coupled via the feedback conductor 14 to the AGC circuit 12 to control the gain thereof in inverse relationship with the amplitude of the QRS wave.

The LTA wave from the low frequency bandpass filter 20 is rectified in a full wave rectifier 34 and coupled to the second input of the comparator 32. The rectifier 34 is triggered by the gating pulse from the QRS trigger circuit 28 so as to provide an input for the comparator 32 only during the QRS interval.

When the rectified LTA signal exceeds the rectified and integrated QRS signal an output appears on conductor 36 which feeds an LTA generator 38. LTA generator 38 then produces a pulse on an output conductor 40, which pulse indicates the presence of a PVC. The conductor 40 is connected to a driver and logic circuit 42 which may provide a visual and/or audible indication of the detection of a PVC and it may also make a record of the number of PVCs occurring within a predetermined period of, say, one minute. For this latter purpose, the gating pulse from the QRS trigger may be coupled to the driver and logic circuit 42 for indicating the occurrence of every QRS interval irrespective of a PVC.

For a more detailed illustration of a preferred embodiment of the present invention, reference is made to FIG. 3. As there shown, the preamplified ECG wave from the patient is applied to the input of the AGC and limiter circuit 12. Preferably this input signal has a level of between 1 and 2 volts but may be in the range of 0.3 volts to 8 volts.

This preamplified signal is introduced to the AGC circuit through a capacitor C1M, and a resistor R1A. This RC combination provides a high-pass pole, with the −3dB breakpoint at slightly less than 1 Hz. The signal then passes through an inverting amplifier, IC1A, whose feedback path is composed of a variable resistance (linear from approximately 15K to 800 Kohms), that is obtained from the output of an optical-electric device. This device consists of a light-emitting diode LED coupled to a photoresistor PR. As the current through the LED increases, the output resistance decreases, and visa versa. The control voltage that supplies current to the LED is developed by the QRS circuits, which will be described later.

The output of amplifier IC1A then passes through a resistor R2A and into another inverting amplifier, IC2A. A plurality of diodes D1A–D4A limit the output of amplifier IC1A to the range of −1.5v to +1.5v, with anything outside these limits being slipped. This feature provides reduced sensitivity to high level bursts of movement or muscle artifact from the patient. The output of the amplifier IC2A is fed into the input of the QRS circuits, and via an attenuation potentiometer P5 to the input of the LTA circuits.

The network composed of a capacitor C1A, a resistor R8A, and a resistor R9A, at the inverting input of an amplifier IC3A, provides for ripple-filtering of the control voltage from the QRS circuits. This control voltage shows up as a positive value at the output of the amplifier IC3A and is used to provide current to the LED in the optical-electric device. A diode D5A allows only positive voltages to pass and provides protection against the LED becoming reverse-biased. Resistors R5A–R7A, along with potentiometer P1 act as a voltage divider, and supply an "idling current" to the LED through amplifier IC3A to keep the output of the photoresistor in its operational region.

The output of the amplifier IC2A is applied to the QRS circuits at the inverting input of an integrated circuit IC1Q, which is a multiple-pole low-pass active filter with poles provided by capacitors C1Q and C2Q and the associated equivalent resistances seen by them. The output of IC1Q is fed to a multiple-pole high-pass active filter IC2Q with poles provided by capacitors C3Q-C5Q, and associated equivalent resistances. The output of the filter IC2Q is then applied to the active bandpass filter IC3Q with a low-pass pole provided by a capacitor C7Q and a resistor R9Q and a high-pass pole provided by a capacitor C6Q and a resistor R8Q. The overall frequency response of these three filters is of an asymmetrically-shaped, bandpass configuration, with the center frequency at around 14 Hz, and −6dB breakpoints at approximately 10 Hz and 17 Hz.

This filter signal, which will be referred to as the QRS signal, is then full-wave rectified by the network composed of resistors R10Q–R13Q, diodes D1Q and D2Q, and integrated circuit IC4Q. This is done in order to avoid any polarity considerations of the ECG signal coming from the patient.

A trigger pulse that goes from +10v to −10v is supplied by the network that includes IC5Q, IC6Q, and transistor T1Q. A voltage divider composed of resistors R14Q and R15Q provides a small voltage to the inverting input of IC5Q and keeps the trigger circuit stable, even if no signal from the patient is present. The output of IC4Q, the full-wave rectified QRS signal, is applied to the noninverting input of IC5Q, and the control voltage developed through IC8Q is applied to the inverting input of IC5Q. When the level of the output of IC4Q exceeds the signal level at the inverting input of IC5Q, a negative pulse is developed, which passes through D3Q and IC6Q, turning transistor T1Q off, allowing the output of IC6Q to go to −10v, and is held there by capacitor C8Q until this capacitor loses its charge. The output of IC6Q then returns to +10v. The rate of discharge of capacitor C8Q, and therefore the trigger pulse duration, is determined by the discharge path through a resistor R17Q and a potentiometer P2 to ground. Potentiometer P2, or a variable resistance switch in its place, is used as an adjustment for setting the duration of the gating pulse. Diode D3Q serves to keep the gating pulse from repeating for a period of approximately 80 to 100 msec. The length of the gating pulse is usually set at around 120 msec for a typical patient.

This gating pulse is applied to the gate of transistor T2Q through R23Q and turns T2Q off every time the pulse arrives. This allows C9Q to pass current, and IC7Q intergrates the signal that is supplied by the output of IC4Q, which is the full-wave rectified QRS signal.

This integral is then ripple-filtered by the network composed of R24Q, R25Q and C10Q, with the control voltage previously mentioned being generated at the output of IC8Q.

From the output of IC2A, the signal is fed through a potentiometer P5 to the input of a multiple-pole bandbass filter IC1L. The purpose of potentiometer P5 is to act as a gain control for the LTA signal. The bandpass filter IC1L is asymmetrically tailored to give a frequency response that is peaked at about 3.5 – 4.0 Hz and has −6dB points at −1.5 Hz and 6 Hz.

Resistors R4L and R5L and potentiometer P3 act as a voltage divider to provide dc offset compensation for the filter IC1L.

The signal is then full-wave rectified by IC2L and LC3L. It should be noted that transistor T1L, an N-channel depletion mode FET in the feedback loop of IC3L, keeps the output of IC3L at zero until a grating pulse arrives from the output of IC6Q. When this happens, transistor T1L goes from its usual ON-state to its OFF-state, allowing the full-wave LTA signal to be seen at the output of IC3L.

Potentiometer P4 and resistor R12L act as a voltage divider to provide dc offset compensation for the full-wave rectifier.

The signal is then fed into a comparator, IC4L, along with the integrated reference voltage developed at the output of IC8Q. When the level of the full-wave rectified LTA signal exceeds the level of the reference voltage, a short duration pulse is seen at the output of IC4L.

This pulse is then differentiated by capacitor C4L and resistor R17L, passes through diode D4L, which allows only positive values to pass, and acts as a trigger pulse for the LTA pulse generator IC5L.

This pulse generator is a one-shot multivibrator and provides a negative-to-positive going pulse of a duration of about 250 msec, this value being adjusted by the time constant of the circuit comprising resistor R16L and capacitor C5L.

From the output of IC5L, the LTA pulse is fed into a suitable driver and logic network for indicating and preferably recording each occurrence of a PVC.

While the present invention has been described in connection with a particular embodiment thereof, it will be understood by those skilled in the art that many changes and modifications may be made without departing from the true spirit and scope of the present invention. Therefore, it is intended by the appended claims to cover all such changes and modifications which come within the true spirit and scope of this invention.

What is claimed is:

1. A method of detecting the presence of premature ventricular contractions by monitoring an ECG signal from a patient comprising the steps of
    passing said ECG signal through an automatic gain control circuit,
    passing the output of said automatic gain control circuit through a high frequency bandpass filter which passes frequencies in the range of about 10 to 17 Hz, and through a low frequency bandpass filter which passes frequencies from about 1.5 to 6Hz,
    rectifying the outputs from each of said filters,
    producing a gating signal during the QRS interval in response to the rectified high frequency signal,
    integrating the rectified high frequency signal during the occurrence of said gating signal,
    controlling the gain of said automatic gain control circuit in response to the integrated high frequency signal, and
    comparing the rectified low frequency signal with the integral of said rectified high frequency signal during occurrence of said gating signal to provide a PVC output signal whenever the rectified low frequency signal exceeds the value of said integral.

2. A method according to claim 1, comprising initiating said gating signal at the beginning of the R wave segment of the QRS complex.

3. A method according to claim 2 wherein said gating signal has a duration of about 120 milliseconds.

4. A method according to claim 1 wherein said automatic gain control circuit comprises
    a light-emitting diode,
    passing through said diode a current having a value dependent on the value of the integral of said rectified high frequency signal during the occurrence of said gating signal, and
    varying the gain of said automatic gain control circuit in inverse relationship to the intensity of the light emitted by said diode.

5. A method according to claim 1 further comprising the step of
    passing said ECG signal through a limiter to reduce the occurrence of PVC output signals in response to high level movement or muscle artifact.

6. A method according to claim 5 comprising the step of
    adjusting the level of the signal applied to said low frequency bandpass filter so that PVC output signals do not occur in response to normal QRS intervals in the ECG waveform.

7. A system for detecting the occurrence of PVCs in an ECG wave, comprising
    a first filter passing frequencies of about 10 Hz and above,-
    a second filter passing frequencies of about 6 Hz and below,
    means coupling said ECG wave to said first and second filters,
    first and second full-wave rectifiers respectively coupled to the outputs of said first and second filters,
    gating pulse generating means responsive to an output from said first rectifier for providing a gating pulse of predetermined duration,
    integrating means coupled to the output of said first rectifier and to which said gating pulse is applied for integrating the output from said first rectifier during the occurrence of said gating pulse, and
    comparator means for comparing the voltage level of the outputs from said integrating means and from second rectifier to provide an output signal when one of said outputs exceeds the other by virtue of a PVC in the ECG wave.

8. A system according to claim 7 comprising
    a limiter having an input to which said ECG wave is adapted to be applied and an output
    an automatic gain control circuit, and
    the output of said limiter being coupled to the signal input of said automatic gain control circuit.

9. A system according to claim 7 comprising
    hold-off triggering means for preventing the initiation of a gating pulse for a period of between 80 and 100 milliseconds after initiation of each gating pulse.

* * * * *